United States Patent [19]

Torii et al.

[11] 4,455,882
[45] Jun. 26, 1984

[54] DEVICE FOR MEASURING A WHOLE DAY URINARY OUTPUT

[75] Inventors: Yoshihiko Torii, Tokyo; Osamu Tochikubo, Yokohama, both of Japan

[73] Assignee: Kabushiki Kaisha Vine, Tokyo, Japan

[21] Appl. No.: 463,552

[22] Filed: Feb. 3, 1983

Related U.S. Application Data

[62] Division of Ser. No. 317,387, Nov. 2, 1981.

[30] Foreign Application Priority Data

Nov. 13, 1980 [JP] Japan ............................. 55-158868
Oct. 15, 1981 [JP] Japan ............................. 56-163394

[51] Int. Cl.$^3$ ............................................. G01N 1/12
[52] U.S. Cl. ............................. 73/864.65; 33/126.4 R; 128/771; 138/89; 141/110
[58] Field of Search ............ 73/864.65, 864.63, 864.64, 73/427, 428; 33/126.4 R; 222/356, 522, 629; 138/89; 141/108, 109, 110, 111, 112; 128/771; 251/347, 353; 604/317, 335

[56] References Cited

U.S. PATENT DOCUMENTS

| | | | |
|---|---|---|---|
| 2,580,711 | 1/1952 | Weidinger | 73/864.65 |
| 2,877,918 | 3/1959 | Gardner | 222/522 |
| 3,318,155 | 5/1967 | Johnson | 73/864.65 |
| 3,371,538 | 3/1968 | Bagby | 73/864.65 |
| 4,055,179 | 10/1977 | Manschot et al. | 604/335 |
| 4,227,413 | 10/1980 | Blum | 73/863.83 |

Primary Examiner—Gerald Goldberg
Assistant Examiner—John E. Chapman, Jr.
Attorney, Agent, or Firm—Fitzpatrick, Cella, Harper & Scinto

[57] ABSTRACT

This invention provides a device for measuring a whole day urinary output, which includes an outer cylindrical container and an inner hollow tubular container to be positioned in the outer cylindrical container for sampling the urinary from the outer container. In one aspect, the inner container is vertically studded in the outer container and both containers are openably-closably communicated with each other at the bottom of the device and the inner container has an openably-closably communicated with the reservoir. In the other aspect, the inner hollow tubular container is a portable sampling tube used in combination with a packing plug. The packing plug has a hollow cylindrical portion and a plug body having a frustoconical head integrally formed with the hollow cylinder and a cylindrical portion underlying the head. The inside diameter of the hollow cylindrical portion is substantially equal to the outside diameter of the sampling tube of which the inside diameter is substantially equal to the outside diameter of the cylindrical portion of the plug. At one opening is provided in the side surface of the hollow cylindrical portion.

3 Claims, 5 Drawing Figures

DEVICE FOR MEASURING A WHOLE DAY URINARY OUTPUT

This is a division of application Ser. No. 317,387, filed Nov. 2, 1981.

BACKGROUND OF THE INVENTION

1. Field of the Invention

This invention relates to a device for measuring a whole day urinary output.

In examining the kidney function, glycosuria, or hypertension, it is required to measure a patient's whole day urinary output as well as the total amount of excretion such as the amount of excreted common salt, the amount of excreted urine sugar or the amount of substances such as urine albumen, creatin, calcium, hormone, etc., present in the urine.

2. Description of the Prior Art

As a container for such purpose, use is generally made of, for example, an open container of about 2 liters formed with a scale, but it is difficult to accumulate and carry such whole day urinary output. Additionally, a space for storing such containers is required and the urine is very ready to evaporate unless the containers are sufficiently sealed; the evaporation of urine gives up an offensive smell and hinders the measurement of the amount of urine and the substances present in the urine.

SUMMARY OF THE INVENTION

The present invention relates to a measure which has been made to overcome such disadvantages and which will take the place of a whole day urinary output container, and intends to provide a small device for measuring a whole day urinary output which does not require a special space for the storage thereof and which does not spoil the sense of cleanliness. The fundamental approach to the present invention starts from the fact that if each urinary output is sampled at a constant rate and the amount of accumulated urine is multiplied by the inverse number of the constant rate, the whole amount of urine can be known without varying the concentrations of various electrolytes and hormones contained in the urine. Thus the present invention has been realized as the result of the study as to how to treat the sampling means.

The principal gist of this invention, which is very simple, is that if, in a double cylindrical container wherein the outer cylinder is in communication with the inner cylinder at the lower end thereof, the area ratio at the same level is constant, the ratio between the amount of liquid in the inner cylinder and the whole amount liquid, when the container is filled with liquid, is equal to the area ratio. This is so because the volume is nothing but the area multiplied by height.

According to a first aspect of the invention, said outer cylinder and inner tubular cylinder are openably-closably in communication with each other at the bottom of the device and the inner tubular cylinder is provided with an openable-closable outlet port for discharging the urine in the tubular cylinder into a reserving chamber.

According to a second aspect of the invention, the inner tubular cylinder is a simple portable urine sampling tube which is, in use, to be put vertically into the outer cylinder for sampling each time a quantity of urine is collected in the outer cylinder. The urine sampling tube is used in combination with a packing plug described later in detail.

BRIEF DESCRIPTION OF THE DRAWING

FIG. 3 showing a cross-section of a packing plug; FIG. 4 showing an inner cylinder, i.e. sampling tube, inserted half-way into a packing plug allowing urine flowing into the sampling tube when the tube together with the plug is put into the outer cylinder; and FIG. 5 showing the sampling tube deeply inserted into the packing plug to block the communication between the sampling tubes and the outer cylinder or container of urine after urine is taken in the sampling tube from the outer cylinder.

DESCRIPTION OF THE PREFERRED EMBODIMENT

Figure 1:
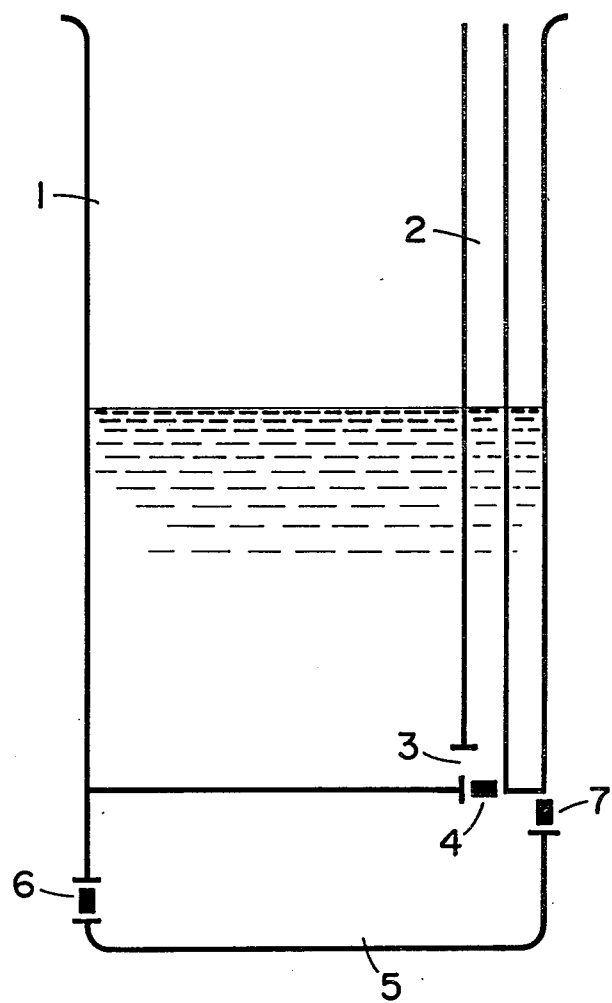
FIG. 1 schematically shows a first embodiment of this invention.
Figure 2:
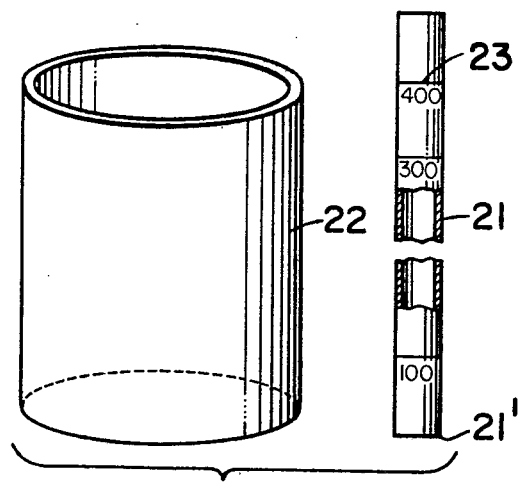
FIGS. 2 through 5 show a second embodiment, FIG. 2 showing an outer cylinder and a sampling tube.
Figure 3:
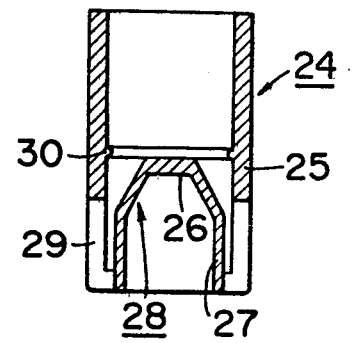
Figure 4:
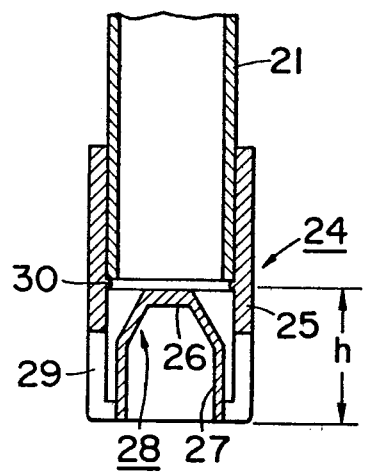
Figure 5:
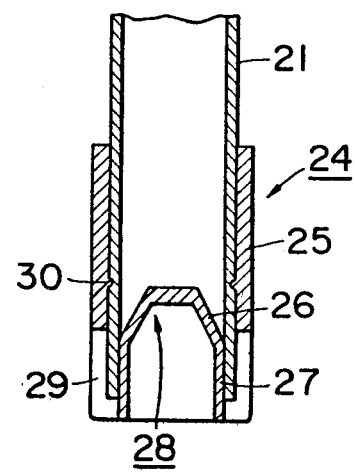

Description of the preferred embodiments will be made referring to the drawing illustrating the first and second embodiments.

The first preferred embodiment is shown in FIG. 1.

The first embodiment is a device for measuring a whole day urinary output comprising a cylindrical container or outer cylinder and a hollow tubular container fixedly positioned in the outer cylinder and having a constant cross-sectional area ratio with respect to said outer container at any vertical locations thereof. The two containers are openably-closably in communication with each other at the bottom thereof, and the tubular container is provided with an openable-closable outlet port for discharging the urine therethrough into a reservoir or chamber. The reservoir can be separated from the outer container but preferably the reservoir is integral with the outer container as shown in FIG. 1. In FIG. 1, reference numeral 1 designates, for example, a beaker-like cylindrical container in which a tubular container 2 is fixed at the bottom of the container 1. This container 2 is in communication with the container 1 at the lower portion thereof through an openable-closable cock 3, and the area ratio of the two containers at the same region (height) is made constant. At the bottom of the tubular container 2, there is an outlet port which also can be opened and closed by means of a cock 4. In this embodiment, a reservoir 5 is integrally formed under the cylindrical container 1 and, in appearance, this measurer looks like a double-bottomed container. This reservoir is provided with an opening-closing port 6 and an air vent plug 7. Although not shown, the reservoir 5 and the cylindrical container 1 or the tubular container, if required, may usually be formed with a scale for indicating the liquid level.

The usage of the above-described measurer will now be described. First, a patient urinates into the container 1 with the cock 3 opened and the other cock 4 closed. At this time, the level of urine in the tubular container 2 is the same as that in the container 1. The cock 3 is then closed and subsequently, the air vent plug 7 is opened, whereafter the cock 4 is opened to let the urine in the tubular container 2 flow down into the reservoir 5, whereafter the cock 4 and the air vent plug 7 are closed and the cock 3 is opened, and then the urine in the container 1 is thrown away. The above-described operation is repeated within a predetermined time. Thus, a predetermined amount of urine is accumulated in the reservoir 5 and therefore, the actual whole amount of urine may be calculated back from said predetermined amount. In this case, the reservoir 5 may be formed with a scale corresponding to the actual amount of urine. If the area in the cylindrical container 1 and the area in the tubular container 2 are selected to a ratio of 9:1, ten times the amount of urine in the reservoir 5 will be the whole amount of urine. If a ratio of 99:1 is selected, one hundred times the amount of urine in the reservoir 5 will be the whole amount of urine. The cocks 3 and 4 may be made by a single two-way cock to be operated from outside of the outer cylindrical container and the vent cock 7 may be provided through the operating shaft of the handle of the two-way cock.

In the above-described example, the reservoir is made integral with the container, but the same result will be obtained even if the reservoir is made separate from the container. When this device is used, the urine during its storage is not in its liberated condition and is thus free of an offensive smell and sense of unpleasantness, and moreover, does not occupy a relatively large space and this is effective.

However, in case of the first embodiment, it is necessary for a patient to operate two cocks or two-way cock and an air vent plug and this sometimes leads to erroneous operation thereof on the part of the patient, and also the fact that the tubular container is vertically fixed in the cylindrical container and cocks are provided to the respective containers leads to a complicated construction and high cost of the entire container.

The second embodiment solves the above-noted problems by a most simple and inexpensive measurer and provides a simple portable tubular device for measuring a whole day urinary output which is free of the offensive smell resulting from evaporation of urine, which does not hinder the measurement of the amount of urine and substances present in the urine, can prevent any erroneous operation by the patient and does not require a large space.

The device for measuring a whole day urinary output according to the second embodiment comprises a combination of a urine sampling tube for sampling urine having two open ends and a packing plug to be attached to at least one of said two ends thereof, said packing plug comprising a hollow cylindrical portion and a plug body having a head of a trapezoidal cross-section disposed in and formed substantially integrally with said hollow cylindrical portion and a cylindrical portion underlying said head, the inside diameter of said hollow cylindrical portion being substantially equal to the outside diameter of said urine sampling tube, the outside diameter of said cylindrical portion of said plug body being substantially equal to the inside diameter of said urine sampling tube, and at least one opening for taking in urine therethrough being provided in the side surface of said hollow cylindrical portion.

The urine sampling tube according to the second embodiment and its packing plug will hereinafter be described referring to FIGS. 2 to 5. The urine sampling tube 21 is a hollow tube open at both ends and formed of a material such as acrylic resin or glass which prevents the urine therein from evaporating. If a colored line 21' or the like is affixed to at least one of the tube ends, it will be convenient because the position of the end of the tube can be observed from outside when urine is sampled with the tube vertically inserted into a urine collecting cup 22. As an example, if the inside diameter of the urine collecting cup 22 is 60 mm$\phi$ and the height thereof is 120 mm and the outside diameter of the urine sampling tube 21 is 8 mm$\phi$ and the inside diameter thereof is 6 mm$\phi$ and the full length thereof is 160 mm, then the ratio of the inside diameter of the cup 22 to the inside diameter of the urine sampling tube 21 is 60:6=10:1, and assuming that the volume of urine collected in the cup 22 at a time is $A_1$, the total amount of urine collected per day is expressed as $$\sum_{n=1}^{n} An.$$

If the urine sampling tube 21 is vertically inserted into the cup 22, the amount of urine entering into the urine sampling tube 21 will be a volume $a_1$ which is 1/100 of $A_1$, and may be expressed as $$\sum_{n=1}^{n} An = 100 \times \sum_{n=1}^{n} an \text{ (ml)}.$$

Accordingly, if a graduation 23 for An is provided on the urine sampling tube 21 and if each urine sampling tube after this urine collection is preserved, the number of times of urination of the examinee or patient per day and the absolute amount of urine per day can be known. For example, about ten urine sampling tubes may correspond to one cup 22, and the number of urine sampling tubes required will be about the same as the number of times per day that the patient urinates. Thus, the patient can carry about ten urine sampling tubes with him.

Description will now be made of a packing plug 24 used for the urine sampling tube. The packing plug 24 comprises a hollow cylindrical portion 25 and a plug body 28 having a frustoconical head 26 disposed in the cylindrical portion 25 and perferably formed integrally therewith and a cylindrical portion 27. The inside diameter of the hollow cylindrical portion 25 is substantially equal to the outside diameter of the previously described urine sampling tube 21, and the outside diameter of the cylindrical portion 27 is substantially equal to the inside diameter of the urine sampling tube 21. At least one opening 29 for introducing urine is provided in the side surface of the cylindrical portion 25. This opening 29 is necessary to maintain the same level of the cup 22 and tube 21 when urine is introduced from the urine collecting cup 22 into the urine sampling tube 21, whereby an equilibrium between the water heads of the urine collecting cup 22 and tube 21 can be achieved. Preferably at least one small projection 30 is provided on the inner periphery of the hollow cylindrical portion 25 so that before collection of urine, the end portion of the urine sampling tube 21 is prevented from further entering into the lower portion of the hollow cylindrical portion 25 by the small projection 30. The position of the small projection 30 is so selected that the tube 21 does not close the opening 29 and that the end portion of the tube 21 is located substantially on the same level as the top of the plug body 28.

The use of the device of the second embodiment will now be described. First, urine is collected in the urine collecting cup 22, and then the cup is placed at such a position that the surface of the liquid therein is substantially horizontal. The urine sampling tube 21 is taken, and by the use of one end of the tube which is to be inserted, preferably having a colored line 21' at the end of the tube, whether this end lies at a proper position in which it is restrained on the small projection 30 is confirmed. Subsequently, the urine sampling tube 21 is vertically inserted into the urine collecting cup 22 with the plug 24 positioned downwardly and while confirming the entry of urine into the tube 21 through the opening 29, the tube 21 is pushed by hand into the plug 24 when the liquid level in the cup becomes substantially flush with the liquid level in the tube, whereupon the tube 21 lowers beyond the small projection 30 and becomes held between the inner side of the hollow cylindrical portion 25 and the outer side of the plug body 28 and reaches the bottom of the cylindrical portion 25 to close the opening 29, thus preventing the communication between the urine in the tube 21 and the urine in the cup 22. Thereafter, the urine sampling tube 21 is removed and a similar or different plug is fitted into the upper open end of the tube 21 to prevent evaporation of the urine therein, thus completing a cycle of operation. The urine remaining in the cup 22 is discarded.

If, in this manner, urine excreted in a day is sampled in a urine sampling tube 21 for each urination and the urine sampling tubes are preserved, the whole amount of urine on that day can be estimated from the total amount of sampled urine. A problem in this case is the error between the estimated amount of urine and the actually measured amount of urine, and such error corresponds to the height h (FIG. 4) of the plug body 28. The result of the measurements carried out by the use of the above-described example, namely, a device in which the urine collecting cup has an inside diameter of 60 mm$\phi$ and the urine sampling tube 21 has an outside diameter of 8 mm$\phi$ and an inside diameter of 6 mm$\phi$ shows that there is an error of about 8% for 50 cc, an error of less than 4% for 100 cc or more, an average error of 6% for 50 to 100 cc, and a general average error of less than 4%, which is a sufficiently practicable error range. Thus, with this taken into account, the urine sampling tube 21 may be provided with a scale.

As described above, the urine sampling device according to the present invention is very convenient in portability and can be sufficiently operated even by patients as well as can reliably prevent evaporation of urine.

We claim:

1. A device for measuring a whole day urinary output comprising an outer cylindrical container and an inner hollow tubular container to be positioned in said outer cylindrical container for sampling urine from the outer cylindrical container characterized in that said inner hollow tubular container is a portable sampling tube used in combination with packing plug to be attached to at least one of the two open ends of the sampling tube, said packing plug comprises a hollow cylindrical portion and a plug body having a frustoconical head disposed in and formed integrally with said hollow cylindrical portion by means of a cylindrical portion underlying said head, the inside diameter of said hollow cylindrical portion is substantially equal to the outside diameter of said urine sampling tube and the outside diameter of the cylindrical portion underlying said head is substantially equal to the inside diameter of the urine sampling tube, and at least one opening for taking-in urine therethrough is provided in the side surface of the hollow cylindrical portion, and the sample tube has a substantially constant cross-sectional area ratio with respect to the outer cylindrical container at any vertical location thereof.

2. A device according to claim 1, further characterized in that at least one small projection is provided on the inner periphery of the hollow cylindrical portion of the plug.

3. A device according to claim 1, further characterized in that a colored line is affixed to at least one of the open ends of the sampling tube.

* * * * *